US008557567B2

(12) United States Patent
Chung et al.

(10) Patent No.: US 8,557,567 B2
(45) Date of Patent: Oct. 15, 2013

(54) METHOD FOR FABRICATING NANOGAP AND NANOGAP SENSOR

(75) Inventors: Bong hyun Chung, Daejeon (KR); Sang kyu Kim, Tsean-gun (KR); Hye jung Park, Daejeon (KR)

(73) Assignee: Micobiomed. Co., Ltd., Daejeon (KR)

( * ) Notice: Subject to any disclaimer, the term of this patent is extended or adjusted under 35 U.S.C. 154(b) by 919 days.

(21) Appl. No.: 11/887,978

(22) PCT Filed: Sep. 5, 2006

(86) PCT No.: PCT/KR2006/003517
§ 371 (c)(1),
(2), (4) Date: Feb. 11, 2009

(87) PCT Pub. No.: WO2007/046582
PCT Pub. Date: Apr. 26, 2007

(65) Prior Publication Data
US 2009/0215156 A1    Aug. 27, 2009

(30) Foreign Application Priority Data

Oct. 21, 2005    (KR) .................. 10-2005-0099585
Aug. 2, 2006    (KR) .................. 10-2006-0072981

(51) Int. Cl.
*C12M 1/34* (2006.01)
*C12M 3/00* (2006.01)
(52) U.S. Cl.
USPC ....... 435/287.2; 435/287.1; 435/6.1; 205/778
(58) Field of Classification Search
USPC .................. 435/6, 287.2, 287.11; 205/778
See application file for complete search history.

(56) References Cited

U.S. PATENT DOCUMENTS

| 6,355,420 B1 * | 3/2002 | Chan ........................... 435/6.12 |
| 6,627,067 B1 * | 9/2003 | Branton et al. ............... 205/778 |
| 6,897,009 B2 | 5/2005 | Johnson, Jr. et al. |
| 7,005,264 B2 * | 2/2006 | Su et al. ....................... 435/6.17 |
| 7,234,184 B2 * | 6/2007 | Yang ................................. 5/712 |
| 7,410,762 B1 * | 8/2008 | Huo et al. .................... 435/6.11 |

(Continued)

FOREIGN PATENT DOCUMENTS

| EP | 1366860 A1 | 12/2003 |
| JP | 12-315786 A | 11/2000 |

(Continued)

OTHER PUBLICATIONS

Hashioka S. et al., "Fabrication Technique for Preparing Nanogap Electrodes by Conventional Silicon Processes" Japanese Journal of Applied Physics, Japan Society of Applied Physics 2005, 44(6A): 4213-4215.

(Continued)

*Primary Examiner* — Melanie Y Brown
(74) *Attorney, Agent, or Firm* — Casimir Jones, S.C.; Tanya A. Arenson

(57) ABSTRACT

The present invention relates to a method of fabricating a nanogap and a nanogap sensor, and to a nanogap and a nanogap sensor fabricated using the method. The present invention relates to a method of fabricating a nanogap and a nanogap sensor, which can be realized by an anisotropic etching using a semiconductor manufacturing process. According to the method of present invention, the nanogap and nanogap sensor can be simply and cheaply produced in large quantities.

12 Claims, 7 Drawing Sheets

(56) References Cited

U.S. PATENT DOCUMENTS

| | | | |
|---|---|---|---|
| 7,947,485 B2* | 5/2011 | Wu et al. | 435/283.1 |
| 8,426,232 B2* | 4/2013 | Sauer et al. | 438/49 |
| 2001/0021534 A1* | 9/2001 | Wohlstadter et al. | 436/518 |
| 2003/0013130 A1* | 1/2003 | Charych et al. | 435/7.1 |
| 2003/0211502 A1 | 11/2003 | Sauer et al. | |
| 2004/0209435 A1* | 10/2004 | Partridge et al. | 438/381 |
| 2005/0074778 A1* | 4/2005 | Letant et al. | 435/6 |
| 2005/0142034 A1 | 6/2005 | Kim et al. | |
| 2006/0014001 A1* | 1/2006 | Zhang et al. | 428/195.1 |
| 2006/0073489 A1* | 4/2006 | Li et al. | 435/6 |
| 2006/0154400 A1* | 7/2006 | Choi et al. | 438/49 |
| 2008/0025875 A1* | 1/2008 | Martin et al. | 422/82.01 |
| 2010/0289505 A1* | 11/2010 | Zhang | 324/663 |

FOREIGN PATENT DOCUMENTS

| | | |
|---|---|---|
| JP | 16-247203 A | 9/2004 |
| JP | 2005-278916 | 10/2005 |
| KR | 2004-57140 | 7/2004 |
| KR | 10-2004-0082418 A | 11/2005 |
| WO | 2004-077503 A2 | 9/2004 |
| WO | 2004-078640 A1 | 9/2004 |
| WO | 2005-069001 A1 | 7/2005 |

OTHER PUBLICATIONS

Storm et al., "Fabrication of Solid-State Nanopores with Single-Nanometre Precision" Nature Materials, Nature Publishing Group London 2003, 2(8): 537-540.

Choi et al., "Sublithographic Nanofabrication Technology for nanacatalysts and DNA chips." J. Vac. Sci. Technol. B 2003, 21(6):2951-2955.

K. Liu, Ph. Avouris, J. Bucchignano, R. Martel, and S. Sun, "A simple fabrication scheme for sub-10nm electrode gaps using e-beam lithography" Appl. Phys. Letters, 80:865 (2002).

Hongkun Park et al., "Fabrication of metallic electrodes with nanometer separation by electromigration." Appl. phys. Lett. 75(2):301-303, 1999.

Chen et al. "Electrochemical approach for fabricating nanogap electrodes with well controllable separation" Appl. Phys. Lett. 86:123105, 2005.

* cited by examiner $Wm = Wo + 2\cotan(\theta) \times Z$

BEFORE

AFTER

METHOD FOR FABRICATING NANOGAP AND NANOGAP SENSOR

TECHNICAL FIELD

The present invention relates to a method of fabricating a nanogap and a nanogap sensor, and, more particularly, to a method of simply fabricating a nanogap and a nanogap sensor at low cost using a semiconductor manufacturing process, with which the position and width of the nanogap can be easily adjusted.

BACKGROUND ART

Generally, a nanogap can be applied to an electrode, so that the nanogap can be used to research the electrical characteristics of a nanoscale structure or can be utilized as a sensor for sensing an extremely small amount of chemical materials or biological materials. Particularly, the nanogap is necessarily used to measure variation in electrical characteristics at the molecular level.

Recently, a method of forming a gap at a predetermined location in a metal wire using an electromigration phenomenon (Appl. Phys. Lett 75, 301), a method of fabricating a nanogap using electron beam lithography (Appl. Phys. Lett 80, 865), a method of forming a relatively large gap and then decreasing the size of the gap using an electrochemical deposition method (Appl. Phys. Lett 86, 123105), a method of fabricating a nanogap using a shadow mask (U.S. Pat. No. 6,897,009), etc. have been proposed as methods of fabricating a nanogap.

However, in the method of forming a nanogap at a predetermined location in a metal wire using a electromigration phenomenon, in which the metal wire having a line width of several tens to several hundreds of nanometers is prepared, a current is caused to flow through the metal wire so that atoms of the metal wire gradually move and thus a predetermined portion of the metal wire is disconnected, thereby forming the nanogap having a width of several nanometers, it is difficult to accurately control the position and size of the nanogap.

Further, in the method of fabricating a nanogap using electron beam lithography, which is a direct patterning method using the electron beam, a precise nanogap can be obtained, but it is difficult to fabricate the nanogap in large quantities.

Further, Korean Patent Application No. 10-2004-0082418 discloses a method of forming a nanogap electrode by placing a spacer on one side of a first electrode, forming a second electrode, and then removing the spacer. However, the method has disadvantages in that the processes therefor are complex, it is difficult to adjust the width of the nanogap, and it is impossible to form a plurality of nanogap electrodes simultaneously.

Further, in the method of forming a nanogap using an electrochemical deposition method, in which metal electrodes, spaced apart from each other by relatively large gaps, are formed on a predetermined substrate, electric terminals are connected to the metal electrode patterns, the entire substrate is dipped into an electrolytic solution, and then voltage is applied thereto, so that an electrode layer is deposited on the surface of the metal electrode pattern, with the result that the electrode layer becomes thick thus gradually decreasing the width of the gap, thereby forming the nanogap therebetween, the processes therein are complex, and it is difficult to adjust the size of the nanogap.

Further, in the method of fabricating a nanogap using a shadow mask, in which a nanostructure such as a nanotube is placed, and then a metal material is deposited thereon, thereby forming a nanogap having the same size as the nanostructure, the size of the formed nanogap depends on that of the nanostructure, and it is difficult to form the nanogap at a desired place.

As such, in consideration of attempts to produce a nanogap using conventional semiconductor process technologies, it has been difficult to economically and efficiently produce the nanogap in large quantities, and thus it has been limited in use to the direct evaluation and analysis of the electrical characteristics of nanoscale materials such as single molecules, nanoparticles, protein and DNA. However, the nanoscale materials have been able to be handled using electrodes having nanoscale gaps due to continuous advancement in semiconductor process technologies. If these technologies are used, it is possible to measure physical or electrical characteristics, such as conductivity etc. of a single molecule or nanoparticles. Moreover, nanoscale electronic devices, such as a nanoscale rectifier and a nanoscale transistor, have been developed by controlling the current flowing through a molecule. Further, research on biotechnology, such as a biological device used to observe the variation in electrical characteristics of protein, DNA and the like when they are placed between the electrodes having nanoscale gaps therebetween and medicine is administered to them, have rapidly advanced. The important technology in the development of molecular electronic devices, biological devices and the like is a technology of forming metal nanogaps having nanoscale gaps, in which nanoscale materials can be secured at desired places.

Accordingly, a technical problem still remaining in the related art is that there is no method of conveniently, economically and efficiently fabricating a nanogap.

DISCLOSURE

Technical Problem

Accordingly, the present invention has been made to solve the above problems, an object of the present invention is to provide a method of conveniently fabricating a nano gap at a low cost using a semiconductor manufacturing process.

Another object of the present invention is to provide a method of fabricating a nanogap sensor which can be used to research the physical and chemical characteristics of a nanoscale material using the nanogap which has been fabricated through the above method.

A further object of the present invention is to provide a method of fabricating a nanogap sensor, which can be used to produce the nanogap sensor, having a predetermined size, in large quantities using the above nanogap and method of fabricating a nanogap sensor.

Still another object of the present invention is to provide a method of observing the electrical and chemical characteristics of nanoscale material using the nanogap sensor fabricated through the above method.

DESCRIPTION OF THE ELEMENTS IN THE DRAWINGS

Figure 1:
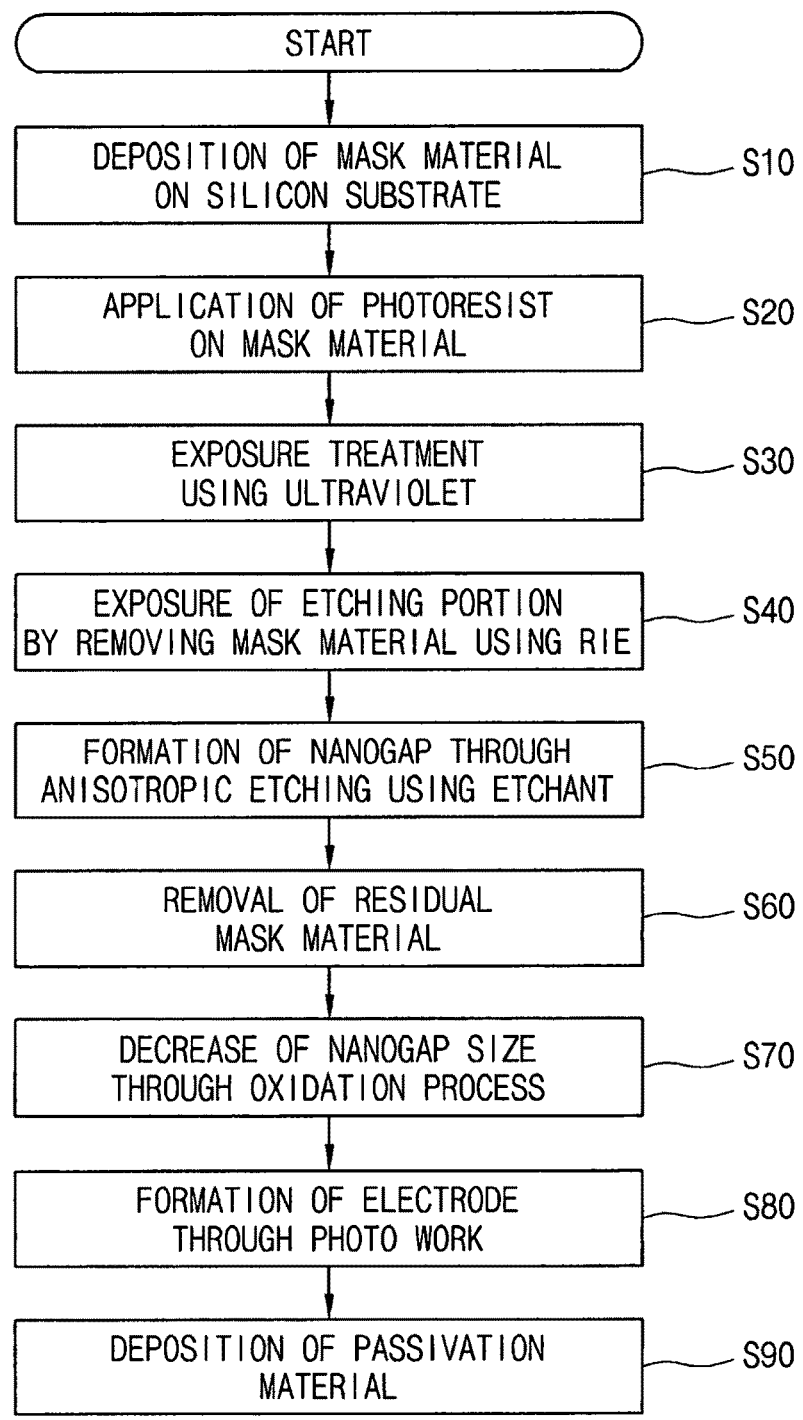
FIG. 1 is a schematic flow chart showing a process of fabricating a nanogap sensor according to an embodiment of the present invention.

10: silicon substrate
20: mask material
30: photoresist
40: buried silicon dioxide
50: electrode material
60: passivation material

BEST MODE

In order to accomplish the above objects, an aspect of the present invention provides a method of fabricating a nanogap, including anisotropically etching a substrate.

Preferably, the anisotropic etching of the substrate includes dry etching or wet etching the substrate to form a V-shaped section (V groove) thereon. More preferably, the anisotropic etching of the substrate includes wet etching using an etchant enabling the anisotropic etching.

The present invention discloses a method of fabricating a nanogap by wet etching a silicon substrate using an etchant enabling the anisotropic etching as a preferred embodiment, but the present invention is not limited thereto. The substrate, which can be used to fabricate a nanogap through the anisotropic etching, may be a silicon substrate, a silicon oxide substrate, a glass substrate, a ceramic substrate or a metal substrate. The metal substrate can be composed of gold, silver, chromium, titanium, platinum, copper, palladium, ITO (indium tin oxide), or aluminum. The nanogap can be fabricated using any the above substrates, which are commonly known in the related art, and with which the nanogap can be fabricated through dry or wet anisotropic etching. In particular, the method of fabricating a nanogap is performed using a semiconductor manufacturing process.

In the semiconductor manufacturing process, a method of forming a pattern through chemical etching has been widely used in the related art to form a desired electronic circuit on a silicon substrate. In this case, the etching is classified as isotropic etching or anisotropic etching in accordance with the way of etching the silicon substrate. The isotropic etching or anisotropic etching can be adjusted depending on the kind of silicon substrate and the kind of etchant for the etching. In the present invention, a method of fabricating a nanogap through the anisotropic etching method is realized as the method of forming a nanogap.

Generally, the term "nanogap" means "a gap" having a width ranging from several nanometers to several tens or hundreds of nanometers in the related art, but the size thereof is not limited to any specific range. As described in detail below, such a nanogap is generally used as a nanogap sensor for evaluating the characteristics of nanoscale molecule or analyzing cells, DNA, protein, or antigen-antibody complexes using a biological device by forming an electrode on the nanogap. According to the present invention, as described in detail below, the desired width of the nanogap can be easily and variously adjusted by adjusting the size of the mask pattern on the silicon substrate in accordance with the analysis object.

According to the preferred embodiment of the present invention, as described above, the nanogap can be easily fabricated at a low cost by applying the anisotropic etching method used in the semiconductor manufacturing process. Further, it is possible to produce the nanogap in large quantities.

The term "anisotropic etching" refers to an etching method in which the etched shape is directional because a specific face of the substrate is etched more rapidly than the other face of the substrate, and the term "anisotropic etching" used in the present invention refers to an etching method of causing a substrate to have a V-shaped section. In contrast, the term "isotropic etching" refers to an etching method in which the substrate is etched such that both side walls of the formed nanogap are perpendicular to the plane of the substrate because the substrate is etched at the same speed in all directions. Accordingly, in the case of anisotropic etching, the width of the portion (gap) that is actually etched on the substrate is much narrower than in the case of isotropic etching, therefore a nanoscale gap can be easily formed.

Silicon has two properties, that is, isotropic etching, having a uniform speed in all crystal directions, and anisotropic etching, having different speeds according to the crystal direction. All types of polycrystal silicon and amorphous silicon exhibit an isotropic property, but single crystal silicon can exhibit different properties, such as isotropy and anisotropy, according to the etching solution. Meanwhile, a <100>, <110>, or <111> type silicon substrate is known as a silicon substrate which is commonly sold, well known and frequently used in the related art. Among these, an anisotropic etching able to form a V-shaped section, which is required in the present invention, is the <100> type silicon substrate. Therefore, at the time of fabrication of the nanogap according to the present invention, it is preferred that this silicon substrate, which can be subjected to the anisotrophic etching, be used. However, in the method of the present invention, any kind of silicon substrate may be used as long as the silicon substrate can be formed into a V-shaped section using anisotropic etching, and it is not limited to the <100> type silicon substrate.

Various etchants commonly known in the related art may be used as a material for performing anisotropic etching of the substrate using the wet etching according to the present invention. These etchants, which are compounds for performing the anisotropic etching, can be manufactured by mixing KOH (potassium hydroxide) with water and isopropyl alcohol, and any one of TMAH (tetramethyl ammonium hydroxide) and EDP (ethylene diamine pyrocatechol) may be used as the etchant. Other than these etchants, any etchant, which can be used to perform anisotropic etching in the related art, such as semiconductor manufacturing technology, may be used to perform the anisotropic etching according to the present invention.

Meanwhile, specifically, a conventional semiconductor manufacturing process used in the present invention to form the nanogap on the silicon substrate may include the step of: depositing a mask material on the silicon substrate; applying a photoresist on the deposited mask material; developing the applied photoresist by performing ultraviolet exposure; exposing a portion of the substrate to be etched by removing the mask material, and removing the residual photoresist; and forming a nanogap by anisotropically etching the silicon substrate to have a V-shaped section (V groove).

In the above process, the step of depositing a mask material on the silicon substrate may be a step of depositing a mask material on the silicon substrate based on the size (width) of a mask pattern calculated from the thickness of the silicon substrate and the size (width) of a desired nanogap. That is, when the size of the desired nanogap, that is, width ($w_o$), is determined in the silicon substrate having a predetermined thickness (z), the width ($w_m$) of a pattern of the mask material deposited on the silicon substrate is determined using the following equation:

$$w_m = w_o + 2\cotan(\theta) \times z \qquad \text{[Equation\_b 1]}$$

In this case, the etching angle ($\theta$) is previously set at a predetermined value according to the silicon substrate.

The width of the nanogap on the silicon substrate fabricated according to the invention can be easily adjusted by adjusting the thickness (z) of the silicon substrate and the width ($w_o$) of the pattern of the mask material using the above equation.

Material, which is not etched by the etchant such as KOH, TMAH or EDP, which are used to anisotropically etch the above silicon substrate, is preferably used as the mask material deposited on the silicon substrate. More preferably, silicon nitride ($Si_3N_4$) may be used as the mask material. However, the mask material is not limited thereto, and any material such as $SiO_2$, which is commonly known and used in the related art, may also be used as the mask material.

As commonly known in the related art, the step of developing the photoresist applied on the mask material is preferably performed using an ultraviolet exposure. The step of removing the mask material, as commonly known in the related art, is performed using an RIE (Reactive Ion Etching) method, by which a portion to be etched is exposed. Then, residual photoresist can be removed through a resist stripping process. The resist stripping process, as commonly used in the related art, includes the steps of removing a photoresist by dipping it into acetone, cleaning the photoresist using methanol, and cleaning the photoresist using distilled water.

After the mask material and residual photoresist are removed, the nanogap according to the present invention can be formed by anisotropically etching the silicon substrate using, preferably, an etchant enabling the anisotropic etching in order to have a V shaped section (V groove). In this case, as described above, the method according to the invention may include the step of etching the silicon substrate using the etchant enabling the anisotropic etching, but is not necessarily limited thereto. That is, it will be obvious to those skilled in the art that the nanogap according to the present invention can be fabricated by etching the silicon substrate using methods commonly known in the related art, such as a dry etching method using O2 or CF4 gas in order to have a V shape. Accordingly, these various modifications, additions and substitutions are included in the scope and spirit of the present invention. In this case, the substrate used in the present invention is not limited thereto, but it is preferred that a <100> type silicon substrate be used in the present invention.

After the nanogap is formed on the silicon substrate through the process described above, a method of fabricating a nanogap according to the invention preferably further includes a step of removing residual mask material from the silicon substrate. The step of removing residual mask material from the silicon substrate may be performed through, preferably, a wet etching method using HF, but is not limited thereto. The residual mask material may be removed through wet or dry etching using any commonly known method. Meanwhile, in the case where the used silicon substrate is a SOI (silicon on insulator) wafer, it is preferred that the method of fabricating a nanogap according to the invention further include a process of removing buried silicon oxide ($SiO_2$) through a wet or dry etching method after the formation of the nanogap, together with the process of removing the residual mask material. In this case, both the residual material and the buried silicon oxide may be removed through the wet etching method using HF.

Figure 4:
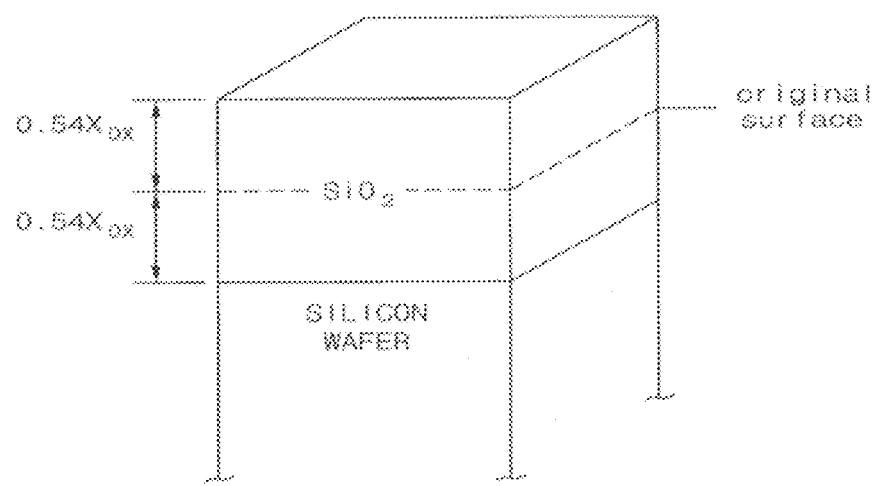
FIG. 4 is a view for elucidating the formation of silicon dioxide on a nanogap in an oxidation process.
Figure 5:
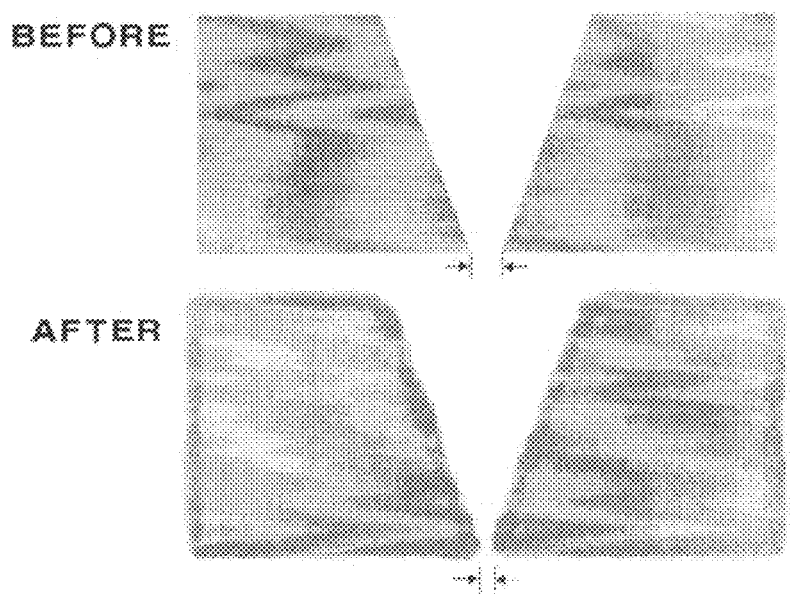
FIG. 5 is a view showing the decrease in gap size after an oxidation process.

In preferable aspect, the method of fabricating a nanogap according to the invention may further include a step of performing an oxidation process, which is a process of decreasing the size (width) of the nanogap, after the step of removing residual mask material from the silicon substrate. As shown in FIG. 5, the width of the nanogap fabricated through the above process can be decreased further through the oxidation process. When the oxidation process is performed, as shown in FIG. 4, there occurs an effect in which silicon dioxide ($SiO_2$) is formed on the silicon substrate and thus the width of the nanogap is decreased. The oxidation process may be performed through dry oxidation in a furnace at high temperature, for example, about 1000° C., and may be performed through wet oxidation, in which the silicon dioxide is rapidly formed in large quantities and the size of the nanogap is thus decreased. The wet oxidation process requires less processing time than the dry oxidation process. In contrast, the dry oxidation process exhibits higher density than the wet oxidation process. Silicon dioxide (SiO2) is formed by reacting silicon atom (Si) with oxygen (O2) due to the injection of oxygen gas in the dry oxidation process. In contrast, silicon dioxide (SiO2) and hydrogen gas (H2) are formed by reacting silicon atom (Si) with water molecules (H2O) using water vapor in the wet oxidation process.

In another aspect, the present invention provides a method of fabricating a nanogap sensor using the nanogap fabricated using the method of fabricating a nanogap according to the invention. Specifically, the method of fabricating a nanogap sensor includes the steps of depositing an insulation material on the substrate on which the nanogap, fabricated using the above method, is formed, and forming a nanogap electrode.

As described above, the nanogap according to the present invention is required to be used as a biological sensor for detecting the molecular characteristics of a biological sample or whether or not a biological samples is present by placing the biological sample, such as a nanoscale molecule, nanoscale cell or antigen-antibody, between the nanogaps. Accordingly, the nanogap sensor of the present invention can be realized by performing a process of forming an electrode, serving as a sensor, on the nanogap and additionally performing a passivation process.

In the method of forming an electrode on the nanogap, the electrode can be formed through a process of depositing a metal used as the electrode and a photo work. In this case, the photo work includes the steps of applying a photoresist, developing the photoresist according to a mask pattern using ultraviolet exposure, removing the metal forming the electrode, and removing the photoresist. The metal used to form the electrode is not limited as long as it has conductivity, and, preferably, is gold, silver, chromium, titanium, platinum, copper, aluminum, palladium, ITO or an alloy thereof. It is preferred that an electron beam deposition method, in which the electron beam has a long mean free path, be employed as the metal deposition process.

After the metal deposition process, a process of passivating portions other than the portion serving as a sensor in the nanogap sensor using a material such as $Al_2O_3$ or SiO2 may further be performed. In the passivation process, a smaller sample is sufficient at the time of measurement using the nanogap sensor because the material is not attached to portions other than the sensor portion in the nanogap sensor. Even in the passivation process, the electron beam deposition method, in which the electron beam has a long mean free path, may be used as the metal deposition process. Materials other than the above materials, which are insulation materials and with which the electron beam deposition can be performed, may be used as the passivation material.

In a further aspect, the present invention provides a nanogap sensor fabricated using the above methods.

In the nanogap sensor according to the present invention, the nanogap sensor includes a voltage-current characteristic, and can detect the variation of current according to the concentration of the object for electrical, chemical, electrochemical or biological analysis, or detect the fact that a binding event occurring between the nanoscale object to be analyzed and a specific bonded structure generates detectable variation in voltage-current characteristics.

The term "nanoscale analysis object" refers to a cell, DNA, protein, an antigen-antibody or enzyme-substrate complex, or the like. Accordingly, the nanogap sensor according to the present invention is preferably used as a biological sensor. In this case, the nanogap sensor can be variously modified depending on the analysis object. For example, when DNA molecule is to be analyzed, the nanogap sensor may be used by securing DNA, both ends of which are provided with a thiol group, to an electrode and then fixing a gold particle etc., to which the DNA can be attached for analysis, thereon. Further, when protein is analyzed, the nanogap sensor may be used by coating the electrode with glass, polymer, or ceramic, attaching a linker such as cysteine to the exposed portion of the electrode, and thus attaching the protein for analysis thereon. Further, when an antigen-antibody reaction is analyzed, the nanogap sensor may be used by bonding a specific antibody to the above linker and then bonding a specific antigen thereto. As such, in the nanogap sensor according to the present invention, the nanogap sensor may be modified by those skilled in the art in various ways depending on the analysis object, and such modifications are included in the scope of the present invention.

Meanwhile, in the nanogap sensor according to the present invention, the analysis object, such as an antibody, can be directly attached to the surface of the electrode formed in the nanogap, either via a linker or without the linker. In contrast, in a conventional nanogap sensor, a method of measuring the analysis object by attaching it to the bottom between the electrodes constituting the nanogap sensor is used. In the nanogap sensor according to the present invention, the analysis object may be measured by attaching it to the bottom between the electrodes. However, as described above, the molecules for measurement can more easily be fixed by directly attaching the analysis object to the electrode, and a smaller amount of sample to be analyzed is thus required, compared to a conventional nanogap sensor. Accordingly, the nanogap sensor according to the present invention, configured so that the analysis object can be directly attached to the electrode of the nanogap, is more useful, compared to the conventional nanogap sensor.

In a further aspect, the present invention provides a method of analyzing the characteristics of a nanoscale material and the electrical and chemical properties thereof using the nanogap sensor according to the present invention fabricated through the above method.

Hereinafter, a method of fabricating a nanogap sensor using a silicon substrate according to an embodiment of the present invention will be described in detail with reference to the accompanying drawings.

Figure 2:
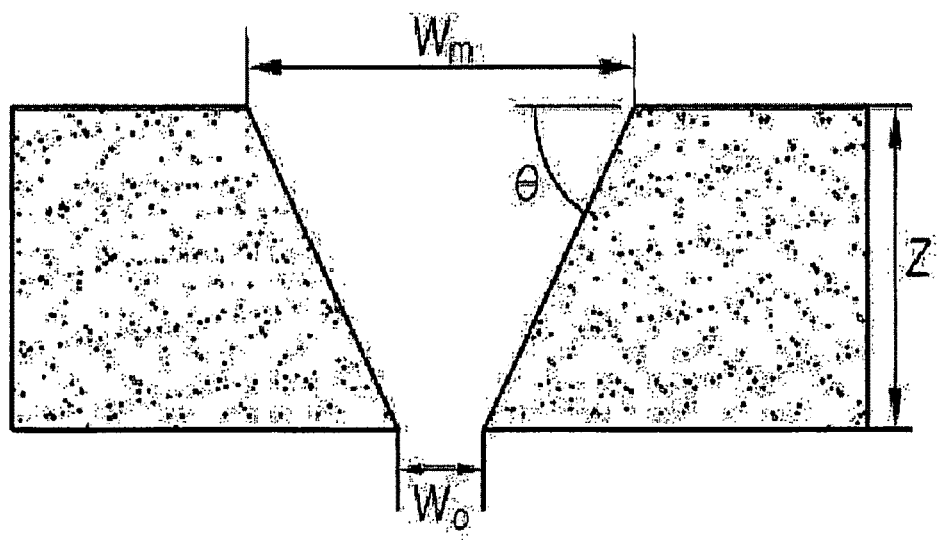
FIG. 2 is a view for mathematically elucidating the determination of gap size (width) based on the thickness of silicon and the width of mask pattern to fabricate a nanogap sensor according to the method of the present invention.
Figure 3:
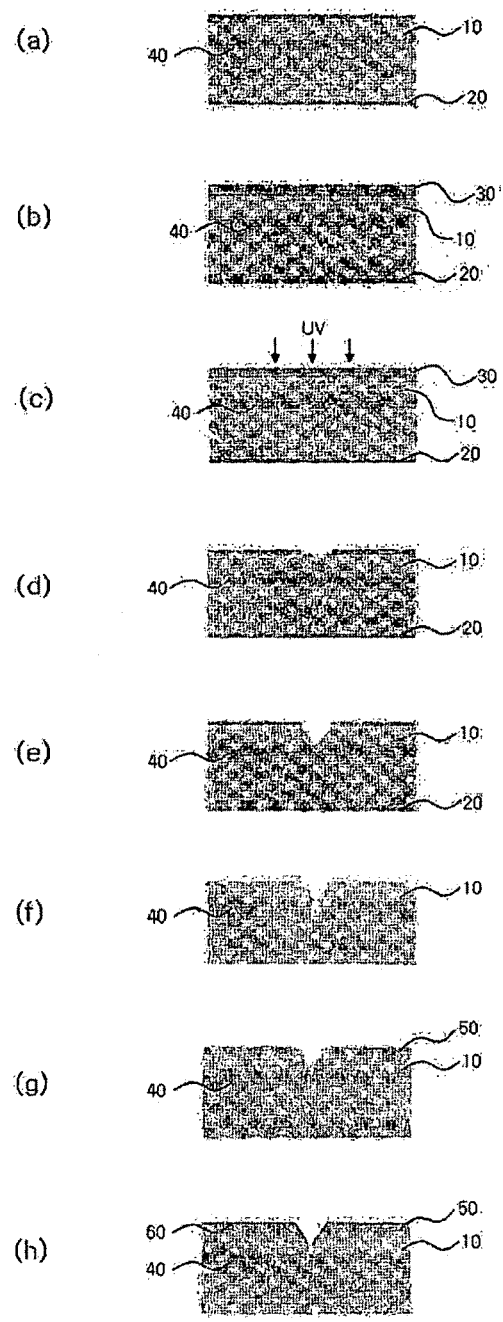
FIG. 3 is a sectional view showing each step of the process of fabricating a nanogap sensor according to an embodiment of the present invention.

FIG. 1 is a schematic flow chart showing a process of fabricating a nanogap sensor according to an embodiment of the present invention, FIG. 2 is a view mathematically elucidating the determination of gap size based on the thickness of silicon and the width of the mask pattern for fabrication of a nanogap sensor according to the method of the present invention, FIG. 3 is a sectional view showing each step of the process of fabricating a nanogap sensor according to an embodiment of the present invention, FIG. 4 is a view elucidating the formation of silicon dioxide on a nanogap in an oxidation process, and FIG. 5 is a view showing a state in which a gap size is decreased, after an oxidation process.

First, as shown in FIG. 2, a mask material 20 is deposited on a silicon substrate 10 based on the size of the mask pattern calculated by the thickness of the silicon substrate 10 and the size of a desired nanogap (S10) (see (a) in FIG. 3). The thickness of the silicon substrate is not particularly limited as long as the silicon substrate is strong enough to allow metal to be deposited thereon in the nanogap sensor. As described above, it is preferred that a <100> type silicon, substrate, which can be anisotropically etched, be used as the silicon substrate 10.

As described above, it is preferred that a silicon nitride ($Si_3N_4$) film or $SiO_2$, which is not etched by an etchant such as KOH, TMAH or EDP for an anisotropic etching, be used as the mask material 20 deposited on the silicon substrate 10.

The mask material 20 is deposited on the silicon substrate 10 through the step 10 (S10), and then a photoresist 30 is applied on the deposited mask material 20 (S20) (see (b) in FIG. 3). Then, the photoresist 30, applied on the mask material 20, is developed by performing ultraviolet (UV) exposure (S30) (see (c) in FIG. 3). The portion of the silicon substrate to be etched is exposed by removing the mask material 20 through RIE (Reactive Ion Etching), and residual photoresist 30 is removed (S40) (see (d) in FIG. 3).

Next, a nanogap having a V-shaped section is formed by anisotropically etching the silicon substrate 10 using the etchant (S50) (see (e) in FIG. 3). In this case, a time required in the etching can be calculated by dividing the thickness of the silicon substrate 10 by the etching rate.

After the nanogap is formed through the anisotropic etching of the silicon substrate 10, residual mask material 20 on the silicon substrate 10 and buried silicon dioxide 40 are removed (see (f) in FIG. 3). In this case, a process for removing the residual mask material 20 and buried silicon dioxide 40 is preferably performed through HF wet etching, but is not limited thereto.

Next, an oxidation process for decreasing the size of the nanogap is performed (S70). FIG. 5 is a view showing a state in which the size of the nanogap is decreased through the oxidation process. When the oxidation process is performed, as shown in FIG. 4, silicon dioxide ($SiO_2$) is formed. In order to decrease the size of the nanogap by rapidly forming a large amount of silicon dioxide, it is preferred that a wet oxidation process be performed.

After the nanogap is performed, an electrode, serving as a sensor, is formed, and then a passivation process is performed. The electrode is formed by depositing the metal used as the electrode on both side walls of the nanogap through a photo work. It is preferred that the process of depositing the metal be performed using an electron beam deposition method, in which the mean free path is long. It is preferred that, after the metal is deposited, the passivation process also be performed by depositing a passivation material using an electron beam deposition method, in which the mean free path is long. The metal used to form the electrode is not limited as long as it has conductivity, and, preferably, is gold, platinum, copper, or an alloy thereof.

Hereinafter, the present invention will be described in detail with reference to preferred examples. However, the present invention is not limited to the following examples, and it will be obvious to those skilled in the art that various modifications are possible within the scope and spirit of the invention.

MODE FOR INVENTION

Examples

Example 1

The Formation of a Nanogap

A <100> type silicon substrate having a thickness of 500 μm and a size of 4 inches was provided, and KOH, which is used as an etchant, was provided. In FIG. 2, θ value is approximately 54.6° (theoretically 54.74°). Therefore, the θ value and the thickness of the silicon substrate were determined, and thus it was determined that the thickness of the photomask was 714 μm using the Equation in FIG. 2, and thus a long rectangular photomask having the above thickness was provided.

$Si_3N_4$, which is only slightly etched by KOH, used as the etchant, was deposited on the provided silicon substrate to a thickness of 200 nm using LPCVD (Low Pressure Chemical Vapor Deposition). Next, a photoresist (AZ5214E, manufactured by Clariant Ltd. in the United States) was applied on the deposited $Si_3N_4$ to a thickness of 2 μm, and then the applied photoresist was developed by performing ultraviolet exposure.

Then, the photoresist having the rectangular pattern was removed, and the $Si_3N_4$ was removed through reactive ion etching, thereby the portion of the substrate to be etched was exposed using the KOH.

Figure 7:
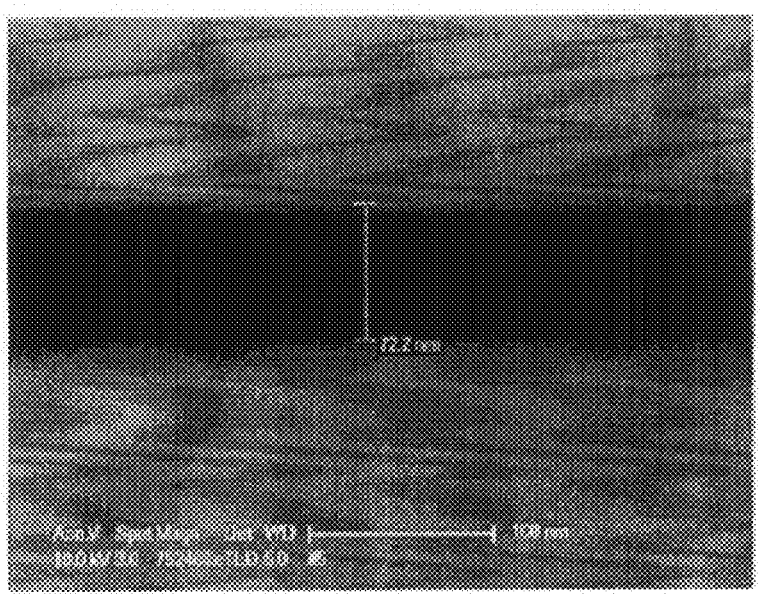
FIG. 7 is an electron microscope photograph showing a gap size in the nanogap in FIG. 6.

Next, the residual photoresist was removed and cleaned, an anisotropic etching was performed using the KOH of 20% at 80° C. for 6 hours in order to obtain a uniform and high etching rate, and thus a nanogap was formed. In this case, the etching rate is approximately 1.4 μm/min. The electron microscope photograph in FIG. 7, as described above, shows the shape of the nanogap formed by performing anisotropic etching using the KOH.

Figure 8:
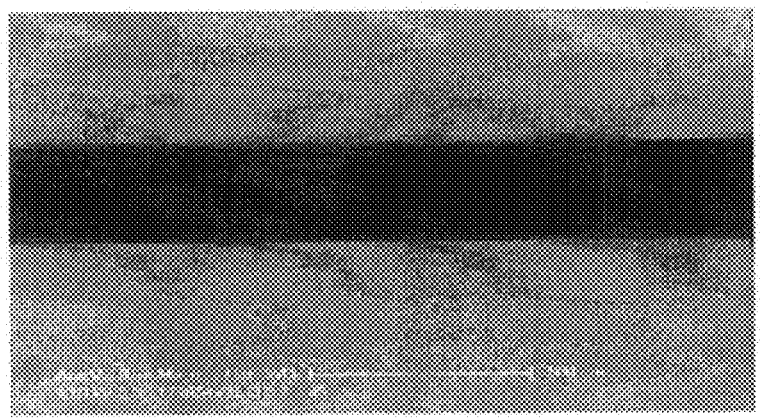
FIG. 8 is an electron microscope photograph of a nanogap, in which the gap size before an oxidation process treatment can be compared with that after the oxidation process treatment, in the nanogap fabricated through a method of fabricating a nanogap according to the present invention.
Figure 8:
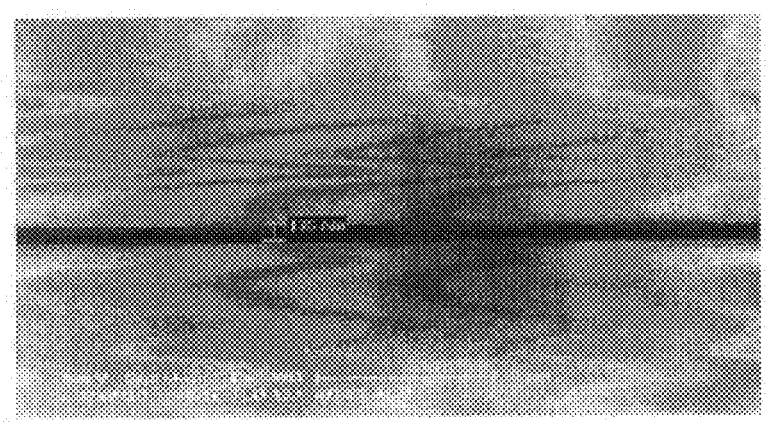

Then, in order to further decrease the size of the nanogap formed through the anisotropic etching, the residual $Si_3N_4$ on the silicon substrate was removed and cleaned through wet etching using HF of 49%, and then dry oxidation was performed in a furnace at a temperature of 1000° C. The electron microscope photograph in FIG. 8 shows that the size of the nanogap was decreased further through this dry oxidation.

Example 2

The Fabrication of a Nanogap Sensor

A <100> type silicon substrate having a size of 4 inches, including top silicon having a thickness of 1 um and buried silicon dioxide having a size of 375 nm, was provided, and KOH was provided. In FIG. 2, a θ value was set at approximately 54.6° (theoretically 54.74°). Therefore, it was determined that the thickness of a photomask was 1.4 μm using the Equation in FIG. 2, and a long rectangular photomask having the above thickness was provided.

$Si_3N_4$, which is only slightly etched by the KOH, used as the etchant, was deposited on the provided silicon substrate to a thickness of 200 nm using LPCVD (Low Pressure Chemical Vapor Deposition). Next, a photoresist (AZ5214E, manufactured by Clariant Ltd. in the United States) was applied on the deposited $Si_3N_4$ to a thickness of 2 μm, and then the applied photoresist was developed by performing ultraviolet exposure. Then, the photoresist having the rectangular pattern was removed, and the $Si_3N_4$ was removed through reactive ion etching, thereby a portion of the substrate to be etched was exposed using the KOH.

Next, the residual photoresist was removed and cleaned, anisotropic etching was performed using the KOH of 20% at 80° C. for 60~90 sec in order to obtain a uniform and high etching rate, and thus a nanogap was formed. In this case, the etching rate was approximately 1.4 μm/min.

Then, in order to further decrease the size of the nanogap formed through the anisotropic etching, the residual $Si_3N_4$ on the silicon substrate was removed and cleaned through wet etching using HF of 49%, and then dry oxidation was performed in a furnace at a temperature of 1000° C.

Figure 6:
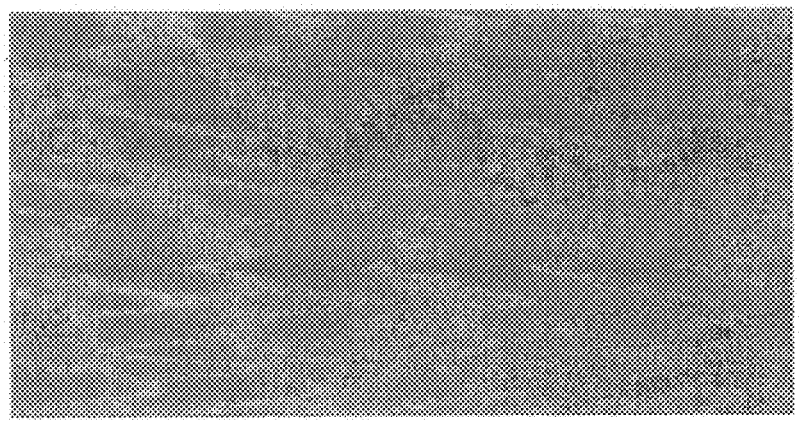
FIG. 6 is an electron microscope photograph of a nanogap obtained through a method of fabricating a nanogap according to the present invention.

FIG. 6 is an electron microscope photograph of the nanogap formed by performing the anisotropic etching using the KOH and then performing the wet etching using the HF.

Next, Cr/Au, which are electrode formation materials, were deposited using an electron beam depositor, and electrodes were formed through photo work, and then the portion other than sensing portion was passivated by depositing $Al_2O_3$ using an electron beam depositor, thereby fabricating a nanogap sensor.

Example 3

The Measurement of Biological Materials Using the Nanogap Sensor

Then, biological materials were measured using the nanogap sensor fabricated in Example 2. First, a linker, which can stably bond with an antibody, was attached to a gold electrode portion exposed from the nanogap sensor, and then an anti-PSA (Prostate Specific Antigen) antibody was bonded thereto. In this case, as disclosed in Korean Patent Application No. 2006-57140, a protein-G linker, N-ends of which are tagged with three cysteines, was used as the linker. There have been examples in which protein-G was modified and then used to stably bond an antibody to a solid support. In the case of the protein-G linker disclosed in Korean Patent Application No. 2006-57140, it was found that the antibody was stably secured by tagging N-end of the protein-G linker with 1-5 cysteines. Particularly, it was found that protein-G bonded with 1-3 cysteines more stably secured the antibody. In this case, the complete protein-G may be used. However, it was found that when only B1 and B2 regions, which are antibody bonding portions, were selected and the N-end thereof was tagged with 1-5 cysteines, the same effect was obtained. Accordingly, in the present invention, the linker, in which the N-end in B1 and B2 regions of the protein-G was tagged with 1-5 cysteines, was used. Since the cysteines tagged to the N-end of the linker have an affinity for gold, they were easily adsorbed on the gold electrode of the nanogap sensor according to the present invention. In the present Examples, anti-PSA antibody were secured on the nanogap sensor provided with this linker, and then PSA was applied thereto to a concentration of 10 ng/ml, 1 ng/ml or 100 pg/ml, thereby the current of the nanogap sensor was measured.

Figure 9:
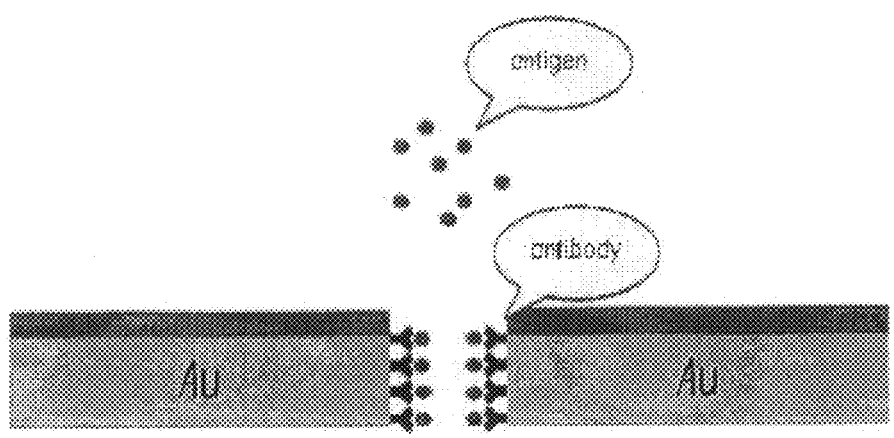
FIG. 9 is a schematic view showing a state in which an antigen is detected by attaching an antibody to a nanogap sensor fabricated according to the present invention.
Figure 10:
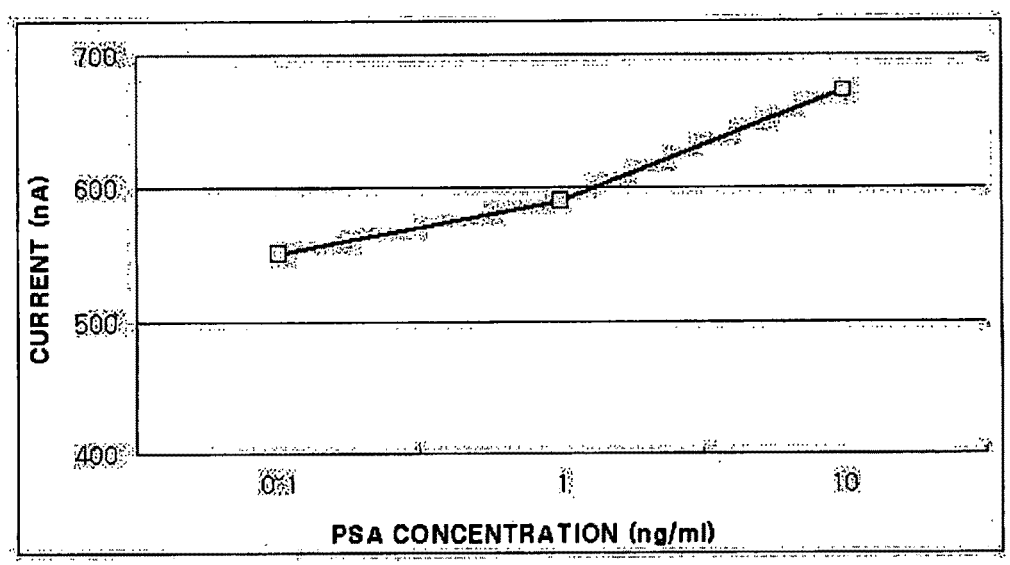
FIG. 10 is a graph showing an experimental result using a nanogap sensor.

FIG. 9 schematically shows the state in which the antibody and antigen are applied on the nanogap sensor fabricated according to the present invention. FIG. 10 is a graph showing the result of measuring current variation with respect to the PSA concentration using the nanogap sensor fabricated according to the present invention.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

As described above, according to the method of fabricating a nanogap and a nanogap sensor, the nanogap and nanogap sensor can be simply and easily produced in large quantities using a semiconductor manufacturing process without using expensive equipment. Accordingly, it is possible to form various electrodes, measure the electrical characteristics of various materials, and apply the electrodes to various sensors.

The invention claimed is:

1. A nanogap sensor for detecting variations of an analysis object in electrical characteristics, comprising:
    a substrate having V-shaped section thereon, the V-shaped section including a top width at a top portion of the substrate and a bottom width at a bottom portion of the substrate in such a configuration that the bottom width has a nano-scaled gap size of several nanometers to several hundreds of nanometers;
    an oxide layer on a surface of the substrate including both sidewalls of the V-shaped section opposite to each other, thereby decreasing the width of the V-shaped section; and
    a pair of electrodes on the oxide layer extending to both of the sidewalls of the V-shaped section to a top surface of the substrate, respectively, the analysis object being attached to each of the electrodes close to the bottom width of the V-shaped section, respectively.

2. The nanogap sensor according to claim 1, wherein the sensor detects variation in chemical characteristics of an analysis object.

3. The nanogap sensor according to claim 1, wherein the sensor detects variation in electrochemical characteristics of an analysis object.

4. The nanogap sensor according to claim 1, wherein the sensor detects variation in biological characteristics of an analysis object.

5. The nanogap sensor according to claim 1, wherein the analysis object is attached to the electrode through a linker attached to a surface of the electrode of the nanogap sensor.

6. The nanogap sensor according to claim 1, wherein the analysis object is a nucleotide, protein, antigen or antibody, or an enzyme or substrate thereof.

7. The nanogap sensor according to claim 6, wherein the antigen is PSA which is a prostate cancer marker.

8. The nanogap sensor according to claim 1, wherein a linker for bonding an antibody is attached to a surface of an electrode of the sensor.

9. The nanogap sensor according to claim 8, wherein the linker is a protein-G, an N-end of which is tagged with cysteine, or a fragment of protein-G, wherein said fragment of said protein-G includes an antibody bonding region of said protein.

10. The nanogap sensor according to claim 9, wherein the linker is a fragment including B1 and B2 regions of protein-G, an N-end of which is tagged with three cysteines.

11. The nanogap sensor according to claim 8, wherein the sensor includes an antibody bonded to the linker.

12. The nanogap sensor according to claim 9, wherein the electrode is made of gold.

* * * * *

UNITED STATES PATENT AND TRADEMARK OFFICE
CERTIFICATE OF CORRECTION

PATENT NO.       : 8,557,567 B2
APPLICATION NO.  : 11/887978
DATED            : October 15, 2013
INVENTOR(S)      : Chung et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1324 days.

Signed and Sealed this
Fifteenth Day of September, 2015

Michelle K. Lee
*Director of the United States Patent and Trademark Office*